(12) United States Patent
Zisapel et al.

(10) Patent No.: US 11,878,016 B2
(45) Date of Patent: Jan. 23, 2024

(54) METHODS AND PRODUCTS FOR TREATING SUBJECTS WITH AUTISM SPECTRUM DISORDERS

(71) Applicant: NEURIM PHARMACEUTICALS (1991) LTD., Tel Aviv (IL)

(72) Inventors: Nava Zisapel, Tel Aviv (IL); Moshe Laudon, Tel Aviv (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 17/937,525

(22) Filed: Oct. 3, 2022

(65) Prior Publication Data
US 2023/0105540 A1 Apr. 6, 2023

Related U.S. Application Data

(60) Provisional application No. 63/251,935, filed on Oct. 4, 2021.

(51) Int. Cl.
| | |
|---|---|
| *A61K 9/20* | (2006.01) |
| *A61K 31/519* | (2006.01) |
| *A61P 25/00* | (2006.01) |
| *A61K 9/107* | (2006.01) |
| *A61K 31/198* | (2006.01) |
| *A61K 31/685* | (2006.01) |
| *A61K 33/06* | (2006.01) |
| *A61K 33/30* | (2006.01) |

(52) U.S. Cl.
CPC .......... *A61K 31/519* (2013.01); *A61K 9/1075* (2013.01); *A61K 9/2013* (2013.01); *A61K 9/2018* (2013.01); *A61K 9/2027* (2013.01); *A61K 9/2054* (2013.01); *A61K 9/2063* (2013.01); *A61K 31/198* (2013.01); *A61K 31/685* (2013.01); *A61K 33/06* (2013.01); *A61K 33/30* (2013.01); *A61P 25/00* (2018.01)

(58) Field of Classification Search
CPC .............. A61K 38/4886; A61K 38/446; A61K 9/0043; A61K 31/14
See application file for complete search history.

(56) References Cited

U.S. PATENT DOCUMENTS

| | | | |
|---|---|---|---|
| 10,614,684 B2 | 4/2020 | Kishore et al. | |
| 2015/0073146 A1* | 3/2015 | Dahanukar | C07C 209/44 544/254 |
| 2018/0214450 A1* | 8/2018 | Kishore | G08B 13/196 |
| 2019/0117577 A1* | 4/2019 | Al Husban | A61K 9/0056 |
| 2020/0254073 A1* | 8/2020 | Kole | A61K 45/06 |

FOREIGN PATENT DOCUMENTS

| | | | | |
|---|---|---|---|---|
| CN | 104434931 A | * | 3/2015 | |
| CN | 105669674 A | | 6/2016 | |
| CN | 105943515 A | | 9/2016 | |
| CN | 110876750 A | * | 3/2020 | |
| EP | 3332769 A1 | * | 6/2018 | ........... A61K 31/519 |
| KR | 102007731 B1 | | 8/2019 | |
| WO | 2021242970 A1 | | 12/2021 | |

OTHER PUBLICATIONS

Garnon et al, Fragile X-related Protein FXR1P Regulates Proinflammatory Cytokine Tumor Necrosis Factor Expression at the Post-trancription Level, 2005, The Journal of Biological ?Chemistry, vol. 280, No. 7, pp. 5750-5763 (Year: 2005).*
Na Young Guk et al: "Strategic approach to developing a self-microemulsifying drug delivery system to enhance antiplatelet activity and bioavailability of ticagrelor", International Journal of Nanomedicine, vol. 14, Feb. 1, 2019 (Feb. 1, 2019), pp. 1193-1212, XP093007293.
Notification of Transmittal of the International Search Report and the Written Opinion issued in PCT/IB2022/059429, dated Dec. 23, 2022, 17 pages.
Bollinger, et al., "Microglial P2Y12 mediates chronic stress-induced synapse loss in the prefrontal cortex and associated behavioral consequences in male mice," Neuropsychopharmacology, (2022). doi: 10.1038/s41386-022-01519-7. Online ahead of print.
Brott, et al., "A peripherally restricted P2Y12 receptor antagonist altered rat tumor incidences with no human relevance: Mode of action consistent with dopamine agonism," Toxicology Reports 1 (2014) 1202-1212.
Oztan, et al., "Neonatal CSF vasopressin concentration predicts later medical record diagnoses of autism spectrum disorder," Proc. Nat. Acad. Sci., (2020) 117:19, 10609-10613.
Parker, et al., "A randomized placebo-controlled pilot trial shows that intranasal vasopressin improves social deficits in children with autism," Sci Transl Med. May 8, 2019; 11(491) (pp. 1-26).
Van Dijck, et al., "Reduced serum levels of pro-inflammatory chemokines in fragile X syndrome," BMC Neurology (2020) 20:138 (pp. 1-12).

* cited by examiner

*Primary Examiner* — Micah Paul Young
(74) *Attorney, Agent, or Firm* — Rothwell, Figg, Ernst & Manbeck, P.C.

(57) ABSTRACT

Methods and products for treating a subject diagnosed with an autism spectrum disorder, an intellectual disability, an anxiety disorder, a mood disorder, a disorder of social interaction, irritability, aggression, self-injurious behavior, hyperactivity, inattention, or Fragile X syndrome or brain neuroinflammation by administering a tablet or liquid or a solid ODT or ODF or SMEDDS containing a ticagrelor or ticagrelor salt or combination with a second agent which may include a magnesium ion containing-compound, a zinc ion containing-compound, a lysine or lysine salt, an arginine or arginine salt, lecithin, or a combination thereof, wherein the ODT or ODF or SMEDDS releases >50% of the ticagrelor or a pharmaceutically acceptable salt thereof and >50% of the second agent within 15 minutes.

28 Claims, 1 Drawing Sheet

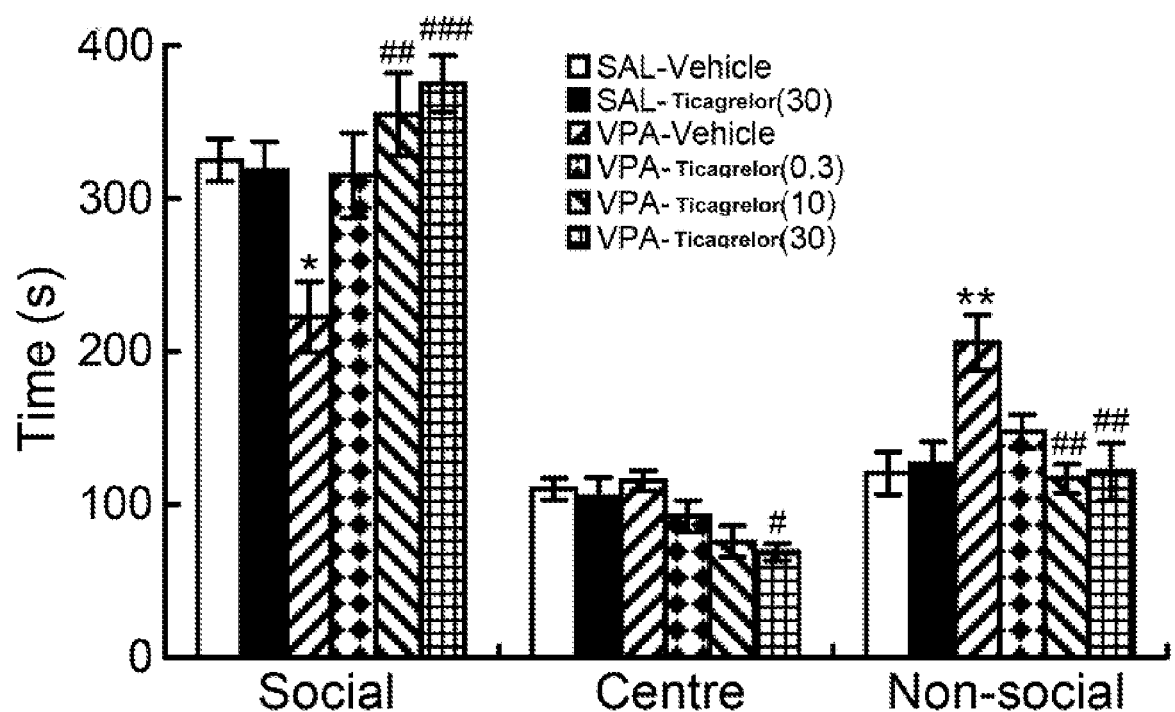

METHODS AND PRODUCTS FOR TREATING SUBJECTS WITH AUTISM SPECTRUM DISORDERS

CROSS-REFERENCE TO RELATED APPLICATIONS

This application claims priority to and the benefit of Provisional Patent Application No. 63/251,935, filed on Oct. 4, 2021, the disclosure of which is incorporated herein by reference in its entirety.

FIELD OF THE DISCLOSURE

This disclosure relates to methods and materials for treating subjects suffering from autism spectrum disorders and associated disorders.

BACKGROUND

Autism or autism spectrum disorder (ASD) is a complex neurodevelopmental condition characterized by persistent difficulties in social interactions and communication, as well as restricted interests and repetitive behaviors. ASD is typically diagnosed during the first three years of life and manifests in characteristic symptoms or behavioral traits (core symptoms). A diagnosis of ASD now includes several conditions that used to be diagnosed separately: autistic disorder, pervasive developmental disorder not otherwise specified (PDD-NOS), and Asperger syndrome. All of these conditions are now encompassed by the diagnostic criteria for autism spectrum disorder as set forth in the American Psychiatric Association's Diagnostic & Statistical Manual of Mental Disorders, Fifth Edition (DSM-V).

Autism may manifest as communication, behavioral, and social challenges that range from mild to severely debilitating in nature. As autism is a wide-spectrum disorder, two individuals with autism may present with very different behaviors, development levels, and health or support needs. Behaviors observed in children and adults with autism may include trouble relating to others or lack of interest in people, extreme sensitivity to certain sounds, smells or lights, repetitive behavior pattern, having narrow obsessive interests, avoiding eye contact, difficulty adapting to changes in routine, and difficulty expressing their needs. Despite advances in early diagnosis and behavior intervention, there is no Food and Drug Administration (FDA)-approved medication specifically targeting core symptoms of ASD (social communication deficits and rigid adherence to routines and repetitive behaviors) to date. The mainstays of treatment for autism are behavioral therapy and educational interventions. The pharmaceutical industry has repeatedly failed in developing an effective treatment for autism, with a string of product failures in recent years including oxytocin, arbaclofen, memantine, and mavoglurant. Clinical trials with the breakthrough-tagged Vasopressin 1a Receptor Antagonist balovaptan (RG7314) to improve social communication in Autism were recently stopped for futility.

Multiple studies report that an abnormal immune function, which includes inflammation, cytokine dysregulation, and anti-brain autoantibodies, can significantly influence the development of autism spectrum disorders. Some individuals may not display outwards signs of infection but instead suffer from subclinical (or asymptomatic) infections (Lintas et al. Association of autism with polyomavirus infection in postmortem brains. J Neurovirol. 2010 March; 16(2):141-9).

There is a long-felt, but unmet need for pharmaceutical products to treat the core symptoms of autism spectrum disorder and autism.

SUMMARY OF THE INVENTION

The present disclosure includes products and methods for treating a subject having disorders of social interaction, anxiety, irritability, aggression, tantrums, rapid changes in mood, self-injurious behavior (SIB), hyperactivity, and inattention in individuals with Autism Spectrum Disorders and associated disorders. In certain aspects, the present disclosure includes administering Ticagrelor or a pharmaceutically acceptable salt thereof in combination with a second agent to the subject. Ticagrelor is also known as (1S,2S,3R,5S)-3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-1,2-cyclopentanediol). The present disclosure also includes an enantiomer of ticagrelor or a pharmaceutically acceptable salt thereof. For example, one enantiomer of ticagrelor is (1R,2R,3S,5R)-3-(7-(((1S,2R)-2-(3,4-Difluorophenyl)cyclopropyl)amino)-5-(propylthio)-3H-[1,2,3]triazolo[4,5-d]pyrimidin-3-yl)-5-(2-hydroxyethoxy)cyclopentane-1,2-diol. Unless stated otherwise, the term ticagrelor should be construed broadly to include enantiomers thereof.

In one aspect, the present disclosure includes a method of treating a subject diagnosed with an autism spectrum disorder, an intellectual disability, epilepsy, an anxiety disorder, a mood disorder, a disorder of social interaction, irritability, aggression, self-injurious behavior, hyperactivity, inattention, Fragile X syndrome or other neuroinflammatory disorders by administering ticagrelor, an enantiomer thereof, or a pharmaceutically acceptable salt thereof alone or in combination with a second agent in a weight ratio of 1:0.1 to 1:50 to the subject.

In one aspect, the present disclosure includes an orally disintegrating tablet (ODT) or an orally dissolving film (ODF) containing ticagrelor, an enantiomer, or a pharmaceutically acceptable salt thereof and a second agent. The ODT and ODF of the present disclosure are solid oral dosage forms. A person of ordinary skill in the art will immediately recognize that an ODT or ODF is a different dosage form than other oral dosage forms, e.g., a chewable tablet or a tablet that should be swallowed whole with liquid, and has different pharmaceutical properties, manufacturing techniques, and regulatory requirements. ODTs and ODFs have specific performance characteristics including rapid oral disintegration in saliva with no need for chewing or drinking liquids to ingest such products.

In one aspect, the present disclosure includes administering ticagrelor, an enantiomer, or a pharmaceutically acceptable salt thereof to a subject in combination with a second agent in the form of an orally disintegrating tablet (ODT).

In one aspect, the present disclosure includes administering ticagrelor, an enantiomer, or a pharmaceutically acceptable salt thereof to a subject in combination with a second agent in the form of an orally dissolving film (ODF).

In one aspect, the present disclosure includes administering ticagrelor, an enantiomer, or a pharmaceutically acceptable salt thereof to a subject or in combination with a second agent in the form of drops, e.g., a self-microemulsifying drug delivery system (SMEDDS).

In one aspect, the present disclosure includes administering ticagrelor, an enantiomer, or a pharmaceutically acceptable salt thereof to a subject in combination with a magnesium salt. In one aspect, the present disclosure includes administering ticagrelor, an enantiomer, or a pharmaceutically acceptable salt thereof to a subject in combination with a zinc salt.

In one aspect, the present disclosure includes administering ticagrelor, an enantiomer, or a pharmaceutically acceptable salt thereof to a subject in combination with lysine. In one aspect, the present disclosure includes administering ticagrelor or a pharmaceutically acceptable salt thereof to a subject in combination with lecithin. In one aspect, the present disclosure includes administering ticagrelor or a pharmaceutically acceptable salt thereof to a subject in combination with lysine and lecithin. In one aspect, the present disclosure includes administering ticagrelor or a pharmaceutically acceptable salt thereof to a subject in combination with lysine and magnesium salt. In one aspect, the present disclosure includes administering ticagrelor or a pharmaceutically acceptable salt thereof to a subject in combination with lysine and zinc salt. In one aspect, the present disclosure includes administering ticagrelor or a pharmaceutically acceptable salt thereof to a subject in combination with an arginine-containing compound.

In one aspect, the amount by weight of ticagrelor in the ODT or ODF or SMEDDS of the present disclosure is lower than in conventional ticagrelor products, e.g., less than 90 mg, less than 60 mg, less than 40 mg, less than 35 mg, less than 30 mg, or less than 10 mg. In one aspect, the amount by weight of ticagrelor to be administered per day according to the methods of the present disclosure are less than for conventional ticagrelor regimens, e.g., less than 90 mg/day, less than 60 mg/day, less than 40 mg/day, less than 30 mg/day, less than 20 mg/day, less than 10 mg/day, or less than 0.25-0.5 mg/kg bodyweight two to four times daily as required. In some aspects, only one ODT or ODF or SMEDDS of the present disclosure is administered per day.

In one aspect, the present disclosure includes administering ticagrelor or a pharmaceutically acceptable salt thereof to a subject in combination with a further component, e.g., an acid that complexes with magnesium or zinc, including but not limited to citric acid, ascorbic acid, threonic acid, tartaric acid, a malic acid, fumaric acid, caprylic acid, gluconic acid, succinic acid, lactic acid, glyceric acid, and/or an alpha-hydroxy-carboxylic acid.

In one aspect, the subject has been diagnosed with Autism Spectrum Disorder.

In one aspect, the subject has an intellectual disability, epilepsy, an anxiety disorder, a mood disorder, a disorder of social interaction, irritability, aggression, self-injurious behavior, hyperactivity, and/or inattention. In one aspect, the subject has Fragile X syndrome.

In one aspect, the subject is an infant, child or adolescent and in such, the amount of ticagrelor to be administered is calculated per body weight, for example 0.01-3 mg/kg, 1 to 3 times a day.

In one aspect, the subject has been diagnosed with elevated TNFα or inflammatory cytokines as markers of neuroinflammation in plasma. Other features and characteristics of the subject matter of this disclosure, as well as the methods of operation, functions of related elements of structure and the combination of parts, and economies of manufacture, will become more apparent upon consideration of the following description and the appended claims, all of which form a part of this specification.

In one aspect, the present disclosure includes administering ticagrelor or a pharmaceutically acceptable salt thereof to a subject with autism spectrum disorder, intellectual disability, epilepsy, an anxiety disorder, a mood disorder, a disorder of social interaction, irritability, aggression, self-injurious behavior, hyperactivity, and/or inattention, Fragile X syndrome or diagnosed with elevated TNFα or inflammatory cytokines as markers of neuroinflammation in plasma.

In another aspect, the ticagrelor and the second agent should be contained in a self-microemulsifying delivery system (SMEDDS) to increase the water solubility of ticagrelor and its bioavailability. For example, in some aspects, the solubility of the ticagrelor formulation is at least 2-fold higher at 25° C. compared to ticagrelor in Brilinta® (commercial product).

The present invention addresses the need for improved ticagrelor dosage forms, particularly low-dosage forms that enable the fast and safe delivery of ticagrelor to brains of subjects suffering from autism spectrum disorders and associated disorders.

BRIEF DESCRIPTION OF THE DRAWINGS

FIG. 1 shows the results of the three-chamber test for time spent in the social area, the centre area, or the non-social area for mice treated with SAL-vehicle, SAL-ticagrelor (30 mg/kg), VPA-vehicle, VPA-ticagrelor (0.3 mg/kg), VPA-ticagrelor (10 mg/kg), and VPA-ticagrelor (30 mg/kg). The bars in FIG. 1 from left to right are in the same order as the labels in the FIGURE legend from top to bottom, i.e., SAL-vehicle is the left-most bar and VPA-ticagrelor (30 mg/kg) is right-most bar.

DETAILED DESCRIPTION

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or embodiments so described.

The singular forms "a," "an," and "the" include plural referents unless the context clearly dictates otherwise.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e., not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e., "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

Generally herein, the term "or" includes "and/or."

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of method steps, active agents, kits, or compositions described with respect to a ODT an ODF or SMEDDS or method of treating a certain subject is intended to and does find direct support for embodiments related to compositions, formulations, ODTs, ODFs, SMEDDS, and methods described in any other part of this disclosure, even if those method steps, active agents, kits, or compositions are not re-listed in the context or section of that embodiment or aspect.

Compositions of the present invention may be administered using any suitable route of administration for the dosage form including but not limited to orally, parenterally (including subcutaneous, intramuscular, intravenous, transcutaneous, subdermal, and intradermal), transmucosally, by inhalation spray, topically, rectally, patch or micropatch, nasally, buccally, vaginally or via an implanted reservoir. In some embodiments, provided compounds or compositions are administrable intravenously and/or intraperitoneally. Suitable dosage forms include, without limitation, a liquid form, a gel form, a semi-liquid (for example, a liquid, such as a viscous liquid, containing some solid) form, a semi-solid (a solid containing some liquid) form, and/or a solid form, for example. Merely by way of example, a tablet form, a capsule form, a food form, a chewable form, a non-chewable form, a slow- or sustained-release form, a non-slow- or non-sustained-release from (e.g., immediate release form), and/or the like, may be employed. Liquid pharmaceutically acceptable compositions can, for example, be prepared by dissolving or dispersing the compounds of the present disclosure in a liquid excipient, such as water, saline, aqueous dextrose, glycerol, or ethanol, or as a SMEDDS. The composition can also contain other medicinal agents, pharmaceutical agents, adjuvants, carriers, and auxiliary substances such as wetting or emulsifying agents, and pH buffering agents.

Preferably, the compositions are administered orally, intranasally, buccally, or sublingually. In some aspects, methods including administering pharmaceutically acceptable compositions in any orally acceptable dosage form including, but not limited to, capsules, tablets, aqueous suspensions or solutions. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Pharmaceutically acceptable compositions of this invention may also be administered by nasal aerosol or inhalation.

In some aspects, pharmaceutically acceptable compositions of this invention are formulated for intra-peritoneal administration.

The present disclosure provides an ODT containing ticagrelor, an enantiomer, or a pharmaceutically acceptable salt thereof and a second agent. In some aspects, the second agent may be a magnesium salt, a zinc salt, lysine, lecithin, or a combination thereof. In some aspects, the ODT may further include a further component including but not limited to citric acid, ascorbic acid, caprylic acid, threonic acid, tartaric acid, malic acid, fumaric acid, gluconic acid, succinic acid, lactic acid, a glyceric acid, an alpha-hydroxycarboxylic acid, amino acid and their magnesium or zinc salts.

The present disclosure also provides an ODF containing ticagrelor, an enantiomer, or a pharmaceutically acceptable salt thereof and a second agent. In some aspects, the second agent may be a magnesium containing-compound, a zinc containing-compound, a lysine (e.g., L-lysine) or lysine salt (e.g., lysine HCl), lecithin, or a combination thereof. In some aspects, the ODF may further include a further component including but not limited to hydrochloric acid, pyrophosphoric acid, tauric acid, sulfuric acid, acetic acid, caprylic acid, carbonic acid, citric acid, ascorbic acid, threonic acid, tartaric acid, a malic acid, fumaric acid, gluconic acid, succinic acid, lactic acid, a glyceric acid, a glyceraldehyde, an alpha-hydroxy-carboxylic acid, amino acid and their magnesium or zinc salts.

In some aspects, the ODT or ODF contains from 5 mg to 200 mg ticagrelor, an enantiomer, or a pharmaceutically acceptable salt thereof. In some aspects, the ODT or ODF contains from 1 mg to 90 mg ticagrelor, an enantiomer, or a pharmaceutically acceptable salt thereof. In some aspects, the ODT or ODF contains from 4 mg to 60 mg ticagrelor, an enantiomer, or a pharmaceutically acceptable salt thereof. In some aspects, the ODT or ODF contains from 4 mg to 50 mg ticagrelor, an enantiomer, or a pharmaceutically acceptable salt thereof. In some aspects, the ODT or ODF contains from 5 mg to 50 mg ticagrelor, an enantiomer, or a pharmaceutically acceptable salt thereof. In some aspects, the ODT or ODF contains from 5 mg to 40 mg ticagrelor, an enantiomer, or a pharmaceutically acceptable salt thereof. In some aspects, the ODT or ODF contains from 2, 3, 4, 5, 6, 7, 8, 9, 10, 15, 20, 25, 30, 35, 40, 45, 50, 55, 60, or 65 mg ticagrelor, an enantiomer, or a pharmaceutically acceptable salt thereof.

In some aspects, the ODT or ODF contains from 1 mg to 300 mg of the second agent. In some aspects, the ODT or ODF contains from 2 mg to 250 mg of the second agent. In some aspects, the ODT or ODF contains from 3 mg to 225 mg of the second agent. In some aspects, the ODT or ODF contains from 4 mg to 200 mg of the second agent. In some aspects, the ODT or ODF contains from 5 mg to 175 mg of the second agent. In some aspects, the ODT or ODF contains from 5 mg to 160 mg of the second agent. In some aspects, the ODT or ODF contains from 6 mg to 150 mg of the second agent. In some aspects, the ODT or ODF contains from 7 mg to 140 mg of the second agent. In some aspects, the ODT or ODF contains from 8 mg to 130 mg of the second agent. In some aspects, the ODT or ODF contains from 9 mg to 120 mg of the second agent. In some aspects, the ODT or ODF contains from 10 mg to 110 mg of the second agent. In some aspects, the ODT or ODF contains from 15 mg to 100 mg of the second agent. In some aspects, the ODT or ODF contains from 20 mg to 80 mg of the second agent. In some aspects, the ODT or ODF contains from 25 mg to 75 mg of the second agent. In some aspects, the ODT or ODF contains from 30 mg to 60 mg of the second agent. In some aspects, the ODT or ODF contains from 35 mg to 55 mg of the second agent. In some aspects, the ODT or ODF contains from 40 mg to 50 mg of the second agent. In some aspects, the ODT or ODF may contain 2 mg to 160 mg lysine. In some aspects, the second agents are between 10% to 50% by weight of the total weight of the ODT or ODF.

In some aspects, the ODT or ODF contains ticagrelor or a pharmaceutically acceptable salt thereof in a ratio of from 1:0.1 to 1:100 to the second agent. In some aspects, the ODT or ODF contains ticagrelor or a pharmaceutically acceptable salt thereof in a ratio of from 1:0.3 to 1:80 to the second agent. In some aspects, the ODT or ODF contains ticagrelor or a pharmaceutically acceptable salt thereof in a ratio of from 1:0.5 to 1:70 to the second agent. In some aspects, the ODT or ODF contains ticagrelor or a pharmaceutically acceptable salt thereof in a ratio of from 1:0.8 to 1:60 to the second agent. In some aspects, the ODT or ODF contains ticagrelor or a pharmaceutically acceptable salt thereof in a ratio of from 1:1 to 1:50 to the second agent. In some aspects, the ODT or ODF contains ticagrelor or a pharmaceutically acceptable salt thereof in a ratio of from 1:1 to 1:40 to the second agent. In some aspects, the ODT or ODF contains ticagrelor or a pharmaceutically acceptable salt thereof in a ratio of from 1:1 to 1:30 to the second agent. In some aspects, the ODT or ODF contains ticagrelor or a pharmaceutically acceptable salt thereof in a ratio of from 1:1 to 1:20 to the second agent. In some aspects, the ODT or ODF contains ticagrelor or a pharmaceutically acceptable salt thereof in a ratio of from 1:1 to 1:10 to the second agent. In some aspects, the ODT or ODF contains ticagrelor or a pharmaceutically acceptable salt thereof in a ratio of from 1:1 to 1:9 to the second agent. In some aspects, the ODT or ODF contains ticagrelor or a pharmaceutically acceptable salt thereof in a ratio of from 1:1 to 1:8 to the second agent. In some aspects, the ODT or ODF contains ticagrelor or a pharmaceutically acceptable salt thereof in a ratio of from 1:1 to 1:7 to the second agent. In some aspects, the ODT or ODF contains ticagrelor or a pharmaceutically acceptable salt thereof in a ratio of from 1:1 to 1:6 to the second agent. In some aspects, the ODT or ODF contains ticagrelor or a pharmaceutically acceptable salt thereof in a ratio of from 1:1 to 1:5 to the second agent. In some aspects, the ODT or ODF contains ticagrelor or a pharmaceutically acceptable salt thereof in a ratio of from 1:1 to 1:4 to the second agent. In some aspects, the ODT or ODF contains ticagrelor or a pharmaceutically acceptable salt thereof in a ratio of from 1:1 to 1:3 to the second agent. In some aspects, the ODT or ODF contains ticagrelor or a pharmaceutically acceptable salt thereof in a ratio of from 1:1 to 1:2 to the second agent. In certain aspects, the ODT or ODF may contain ticagrelor or a pharmaceutically acceptable salt thereof in a ratio of from 1:0.1 to 1:10, 1:0.4, 1:2, or 1:4 to lysine.

In some aspects, the ODT or ODF contains lysine or a lysine salt as the second agent. In some aspects, the ODT or ODF contains lecithin as the second agent. In some aspects, the ODT or ODF contains a combination of lysine and lecithin as the second agent.

In some aspects, the ODT or ODF contains ticagrelor as a free base or an acid addition salt of ticagrelor. In some aspects, acid addition salt of ticagrelor is any pharmaceutically acceptable acid addition salt. In some aspects, acid addition salt of ticagrelor includes, for example, ticagrelor hydrochloride, ticagrelor tartrate, ticagrelor threonate, ticagrelor glycerate, ticagrelor citrate, or ticagrelor fumarate.

In some aspects, the ODT or ODF contains one or more magnesium salts or magnesium compounds or zinc salts or zinc compounds. In some aspects, the ODT or ODF contains a bromide, an iodide, or a complex of magnesium or zinc compounds with hydrochloric acid, pyrophosphoric acid, tauric acid, sulfuric acid, acetic acid, carbonic acid, citric acid, ascorbic acid, threonic acid, tartaric acid, a malic acid, fumaric acid, gluconic acid, succinic acid, lactic acid, a glyceric acid, a glyceraldehyde, an alpha-hydroxy-carboxylic acid, amino acid and their magnesium or zinc salts. In some aspects, the second agent or salt is not a threonate-containing compound (e.g., not a magnesium threonate). In some aspects, the second agent or salt is not a stearate-containing compound (e.g., not a magnesium stearate).

ODTs are typically produced as a single unit form or a multiunit system in which a plurality of particles, each containing an active ingredient, are compressed into a single dosage form. Conventional methods for manufacturing ODTs can result in tablets, which are soft, friable, and unsuitable for packaging in typical blister packs or bottles. Thus, designing ODTs as multiunit system, which are stable during manufacturing and storage and also have acceptable friability, remains a challenge.

A pharmaceutical composition may be in the form of an orally disintegrating tablet (ODT), e.g., a compressed ODT. The term "orally disintegrating tablet" as used herein refers to a tablet which substantially disintegrates in an oral cavity of a subject in need thereof within less than a certain time after administration. The disintegration can be measured in vitro using e.g., the USP <701> Disintegration Test, which is incorporated herein by reference. Additionally, "orally disintegrating tablet" can refer to a loss of structural integrity of the tablet following administration to the buccal cavity of a subject when in contact with the mucosal tissue of the tongue, cheek, and/or mouth. The orally disintegrating tablet is typically placed on the tongue (lingual administration) which stimulates saliva generation and enhances disintegration of the composition. In some aspects, the ODT may contain one or more populations of granules, beads, pellets, or powder containing one or more active ingredients and/or excipients described herein.

A pharmaceutical composition of the present disclosure may be in the form of an ODF. An ODF according to the present disclosure dissolves in about 1 second to about 60 seconds in the mouth of a human subject, e.g., within 5 to 50 seconds, 10 to 40 seconds, or 15 to 30 seconds. An ODF according to the present disclosure has high flexibility, wettability, and is non-irritating to oral mucosa.

An ODF according to the present disclosure may contain a plurality of layers. One or more active ingredients may be contained in each layer of the ODF. In some aspects, one or more polymers, buffers, or acids may be provided in one or more layers of the ODF of the present disclosure.

An ODF according to the present disclosure may have a thickness of from 0.01 to 10 mils. An ODF according to the present disclosure may have a thickness of from 10 to 200 microns.

An ODF according to the present disclosure may have regions of differing dissolution rates. An ODF according to the present disclosure may contain polymers including, but are not limited to ethyl cellulose, hydroxypropyl ethyl cellulose, cellulose acetate phthalate, hydroxypropyl methyl cellulose phthalate, acrylic polymers, vinyl acetate, sodium sulphonated polyesters, carboxylated acrylics, trimethylpentanediol/adipic acid/glycerin cross polymer, polyglycerol diisostearate/IPDI copolymer, carboxylated vinyl acetate copolymer, vinylpyrrolicone/vinyl acetate/alkylaminoacrylate terpolymers, vinylpyrrolidone/vinyl acetate copolymer, cellulose acetate phthalate, hydroxypropyl methylcellulose phthalate, polyvinylacetate phthalate, poly(ethylacrylate methacrylic acid) copolymer, shellac, hydroxypropyl methylcellulose acetate succinate, poly(methyl vinyl ether/maleic acid) monoethyl ester, poly(methyl vinyl ether/maleic acid) n-butyl ester, hydroxypropylmethyl cellulose (HPMC), hydroxypropyl cellulose (HPC), pullulan, carboxymethyl cellulose (CMC), pectin, starch, polyvinyl acetate (PVA), polyvinyl pyrrolidone (PVP), a polyvinyl alcohol-polyethylene glycol graft copolymer, propylparaben sodium, methylparaben sodium, Crospovidone, Croscarmellose sodium, Polyvinylpyrrolidone, sodium alginate, a polyalkylene glycol, a polyalkylene oxide, a polyethylene glycol (PEG), xanthan gum, tragacanth gum, guar gum, acacia gum, arabic gum, polyacrylic acid, methylmethacrylate copolymer, carboxyvinyl polymer, polymers of acrylic acid and C10-C30 alkyl acrylate crosslinked with allyl pentaerythritol, a starch, microcrystalline cellulose, amylose, high amylose starch, hydroxypropylated high amylose starch, dextrin, pectin, chitin, chitosan, levan, elisan, collagen, gelatin, zein, gluten, soy protein isolate, sodium stearyl fumarate, whey protein isolate, casein, plasticizers, sweetening and flavoring agents, coloring agents, saliva-stimulating agents, and thickening agents. Polymeric materials are present in amounts ranging from about 0.1% to about 99%, e.g., from about 10% to about 90%, from about 20% to about 80%, from about 30% to about 70%, or from about 40% to about 65%. The molecular weight of the polymeric materials may range from about 1,000 to 900,000, more specifically from about 5,000 to 600,000, 7,000 to 400,000, 10,000 to 200,000, 12,000 to 100,000, or 15,000 to 80,000. The ODT or ODF may also contain one or more solvents. Solvents include but are not limited to an organic or inorganic solvent, a polar organic solvent, a non-polar organic solvent, water, an alcohol, methylene chloride, or a sugar alcohol. In some aspects, a sugar alcohol may include allitol, arabitol, dextrose, dulcitol, erythritol, galactitol, glycol, glycerol, iditol, isomalt, lactitol, maltitol, mannitol, sorbitol, threitol, xylitol, and combinations thereof. Plasticizers may include, but are not limited to, benzyl benzoate, chlorobutanol, dibutyl sebacate, diethyl phthalate, glycerol, polyethylene glycol, propylene glycol, sorbitol, triacetin and triethyl citrate. Additional optional ingredients may include taste modifiers, such as flavorants, sweeteners, and taste-masking agents; colorants; polyglycols, such as polyethylene glycol, propylene glycol and glycerol; chelating agents to prevent oxidation such as ethylenediaminetetraacetic acid (EDTA); fillers such as sorbitol, mannitol, sucrolose, lactitol, erythritol, maltitol, lactose, sucrose, xylitol, silica, a dextrate, glucose, fructose, saccharin and its various salts such as the sodium salt; dipeptide sweeteners such as aspartame; dihydrochalcone compounds, glycyrrhizin, Stevia Rebaudiana (Stevioside), chloro derivatives of sucrose such as sucralose, sugar alcohols, sugars and trehalose, and emulsifiers such as surface and release modifiers including, but not limited to, castor oils, cetyl alcohol, and hydrogenated vegetable oils. Sweeteners may include but are not limited to soluble saccharin salts (e.g., sodium and calcium salts); the free acid form of saccharin; cyclamate salts; aspartame; and the potassium, calcium, sodium, and ammonium salts of 3,4-dihydro-6-methyl-1,2,3-oxathiazine-4-one-2,2-dioxide.

A pharmaceutical composition may be in the form of an orally administered SMEDDS for increasing the bioavailability of poorly water-soluble drugs or pharmaceutical compositions. The SMEDDS formulation generally includes an emulsion including an oil or lipid material, a surfactant, and a hydrophilic co-surfactant. A poorly water-soluble drug or pharmaceutical is emulsified in the self-microemulsifying excipient formulation thereby increasing the in vivo bioavailability of the drug or pharmaceutical formulation. Additionally, poorly water-soluble drugs, like ticagrelor, can be treated according to the present invention and can then be used in combination with other drugs and/or pharmaceutical ingredients which may or may not be poorly water-soluble.

SMEDDS pharmaceutical compositions of the invention may be formulated for oral administration of ticagrelor, e.g., emulsions, aqueous or oily suspensions, filled hard or soft capsules or syrups (50-300 mg ticagrelor/ml) or prepared powders or granules, troches, tablets or lozenges. Pharmaceutically acceptable carriers or additives for formulation into formulations such as tablets and capsules include binders such as lactose, saccharose, sorbitol, mannitol, starch, amylopectin, cellulose or gelatin; Excipients such as dicalcium phosphate; Disintegrants such as corn starch or sweet potato starch; Glidants such as magnesium stearate, calcium stearate, sodium stearyl fumarate.

The oil phase of the self-microemulsifying formulation includes one or more lipids or glycerides containing compounds such as caprylic/capric acid glycerides but can also include other suitable oil phase compounds, for example, polyoxylglycerides, isopropyl myristate, isopropyl palmitate, triglycerides, propylene glycol derivatives, and glyceryl monooleate.

Suitable surfactants or emulsifying agents used in the self-microemulsifying formulation of the present invention include polyoxyethylene castor oil derivatives, caprylocaproyl macrogol glycerides, sorbitan derivatives, polyoxyethylene alkyl ethers, polyoxyethylene sorbitan fatty acids, polyoxyethylene-polyoxypropylene copolymers and other suitable surfactants, for example, long alkyl chain sulfonates/sulfates such as sodium dodecylbenzene sulfonate, sodium lauryl sulfate, and dialkyl sodium sulfosuccinate, quaternary ammonium salts, fatty alcohols such as lauryl, cetyl, and steryl, glycerylesters, fatty acid esters, and polyoxyethylene derivatives thereof.

Co-surfactants suitable for use with the self-emulsifying excipient formulation of the present invention may contain one or more selected from the group consisting of tetraglycol, propylene glycol, diethylene glycol monoethyl ether, and polyethylene glycol and alcohols of intermediate chain length such as hexanol, pentanol, and octanol which are known to reduce the oil/water interface and allow the spontaneous formulation of the emulsion.

The method of making a drug delivery system for increasing the bioavailability of a drug and/or pharmaceutical ingredient or formulation by emulsifying the drug with the self-microemulsifying excipient formulation of the present invention includes the steps of solubilizing ticagrelor and additional ingredients in a mixture of surfactant, co-surfactant and oil. The emulsion can then be added to a suitable dosage form such as liquid drops, soft or hard-filled gelatin capsules and allowed to cool.

The relative proportions of surfactant and co-surfactant in the self-microemulsifying formulation of the present invention can influence the solubilizing and dissolution properties of the formulation. In some aspects, the emulsion composition may contain about 10 to 50% by weight of oil, 5 to 80% by weight of surfactant and 5 to 80% by weight of the co-surfactant based on the total weight of the emulsion composition and the self-emulsifying drug delivery system characterized in that it contains an emulsion composition and ticagrelor in a weight ratio of 15:1 to 3:1.

Solid formulations of the present disclosure are palatable, e.g., have acceptable organoleptic properties such as good taste and mouthfeel to maintain patient compliance or adherence to the dosing regimen, while also providing the disclosed pharmacokinetic and bioavailability characteristics to provide the desired therapeutic effect. Taste-masking components can inhibit or delay drug release and decrease drug solubility, thereby providing unacceptable pharmacokinetic properties. Conversely, components of the formulation that promote rapid release may result in undesirable taste or mouthfeel properties. Accordingly, an acceptable solid ODT or ODF formulation must balance these contradictory characteristics in order to provide a palatable (e.g., taste-masked), fast disintegrating composition with acceptable pharmacokinetics.

In some embodiments, the oral dosage forms of the present disclosure may contain at least one of hydroxypropyl methylcellulose, hydroxypropyl cellulose, polyvinylpyrrolidone, carrageenan, polyethylene glycol, polyvinyl alcohol or a mixture or combination thereof. The ODTs may contain a core, a subcoating, and/or a coating In some aspects, the active ingredients are encapsulated, e.g., in a matrix, layer, polymer, gel-forming region, and/or gel. Stabilization may be provided such that impurity levels when measured after placing the orally disintegrating tablet under accelerated storage conditions at 40° C. and 75% relative humidity for 1-3 months are below requisite pharmaceutically acceptable specifications thereby being suitable for commercial use In some embodiments, the ODT has been produced by mixing the ticagrelor or a pharmaceutically acceptable salt thereof with the second active agent in a liquid solution or suspension, filled into a mold, and freeze-dried. In some aspects, the ODT or ODF of the present disclosure is produced aseptically. In some aspects, the ODT or ODF of the present disclosure is terminally sterilized.

In some embodiments, the ODT may be coated with a coating. In certain embodiments, the enteric coating applied to the cores comprises one or more of hydroxypropyl methylcellulose phthalate (HPMCP), hydroxypropyl methylcellulose acetate succinate (HPMCAS), polyvinyl acetate phthalate, cellulose acetate trimellitate, cellulose acetate phthalate (CAP), shellac, polymethacrylic acid, polymethyl methacrylate, polyethyl methacrylate, polyethyl acrylate or a mixture or combination thereof, with each possibility representing a separate aspect. In various embodiments, the plurality of cores are further coated with a subcoating as an undercoat to the enteric coating and/or a coating comprising a reverse enteric polymer as an overcoat to the enteric coating. Each possibility represents a separate embodiment. In particular embodiments, the subcoating applied to the cores comprises one or more of hydroxypropyl methylcellulose, hydroxypropyl cellulose, polyvinylpyrrolidone, polyethylene glycol, polyvinyl alcohol or a mixture or combination thereof, with each possibility representing a separate aspect.

In some embodiments, the ODT of the present invention includes a water-soluble polymer, a combination of two or more water-soluble polymers or a combination of a water-soluble polymer and a water-insoluble or poorly-soluble polymer. Water soluble polymers that may be used in the orally dissolving formulations of the present invention include, but are not limited to, cellulose derivatives, synthetic polymers polyacrylates and natural gums. For example, the water soluble polymers used in the orally dissolving formulations of the present invention may include, but are not limited to, methyl cellulose, hydroxypropyl cellulose, hydroxypropylmethyl cellulose, ethyl cellulose, hydroxyethyl cellulose, hydroxypropyl cellulose, carboxymethyl cellulose, cellulose acetate phthalate, cellulose acetate butyrate, amylose, dextran, casein, pullulan, gelatin, pectin, agar, carrageenan, xanthan gum, tragacanth, guar gum, acacia gum, arabic gum, polyethylene glycol, polyethylene oxide, polyvinyl pyrrolidone, polyvinyl alcohol, cyclodextrin, carboxyvinyl polymers, sodium alginate, polyacrylic acid, methylmethacrylate or mixtures thereof.

In particular embodiments, the concentration of the water-soluble polymer in the formulation may be about 20% to about 90% (by weight), or between about 40% to about 80% (by weight). The above polymers can be used to coat the ODT. The coating can function as a taste-masking barrier (i.e., over particles of the drug contained within the ODT), and also can protect components from atmospheric degradation and improve appearance. In the instance where this coating may retard the disintegration, rapid disintegration agents can also be included in the composition. The use of disintegrating agents such as dried starch, sodium alginate, lactose, sodium bicarbonate, calcium carbonate, polyvinyl pyrrolidone, microcrystalline cellulose and the like in the tablet core or granulation mixture of a swallowable tablet formulation is known. Such elements can be used in combination with polymeric coatings to enhance the disintegration. In addition, any of the disintegration agents known in the skill of art can be used to improve the disintegration of ODTs and dissolution of ticagrelor and the second agent when they are coated with polymers.

A compressed ODT may include a disintegrant, e.g., in an amount of about 2% to about 25% by weight of a total tablet weight. In certain embodiments, the ODT may contain one or more additional excipients. Such excipients may be selected from the group consisting of a binder, a filler, a diluent, a surfactant, a glidant, a lubricant, a plasticizer, an anti-tacking agent, an alkaline substance, a tonicity enhancing agent, a wetting agent, a buffering substance, a preservative, a flavoring agent, an opacifier, a colorant, an anti-oxidant or a mixture or combination thereof in an amount of not more than about 50% by weight of a total tablet weight.

An excipient may be a distributing agent, e.g., colloidal $SiO_2$, fumed silica, diatomaceous earth, kaolin, talc, and/or magnesium aluminum trisilicate.

Suitable examples of lubricants include but are not limited to talc, sodium stearyl fumarate, calcium stearate, magnesium stearate, zinc stearate, glyceryl behenate and glyceryl monostearate. Preferred lubricant for the composition of the present invention is sodium stearyl fumarate or magnesium stearate or combination thereof. In some aspects one or more lubricants may be included in an amount of about 0.1 to 5% by weight of the solid dosage form of the present disclosure.

Optional effervescent compounds include compounds which evolve gas. For example, gas may be evolved by means of a chemical reaction between soluble acid source, an alkali monohydrogencarbonate or other carbonate source and water and/or saliva in the mouth. The gas produced by such a chemical reaction may be carbon dioxide. The acid source may be any which are safe for human consumption and may include edible acids, such as, for example citric acid, tartaric acid, malic acid, fumaric acid, adipic acid, succinic acid and the like. Carbonate source includes dry solid carbonate and bicarbonate salts for example sodium carbonate, sodium hydrogen carbonate, magnesium carbonate, calcium carbonate and the like. The preferred effervescent couple for the present invention is citric acid (anhydrous)/sodium hydrogen carbonate. In some aspects one or more effervescent compounds may be included in an amount of about 1 to 30% by weight of the solid dosage form of the present disclosure.

In some embodiments, the orally dissolving formulations according to the present invention may include surfactants including, but not limited to, sodium docusate, polyoxyethylene ether, a poloxamer, polysorbates (Tween), glyceryl monostearate, polyoxyethylene stearates, sodium lauryl sulfate, sorbitan esters and combinations thereof. If present, the surfactant may be included in the formulation from about 0.1% to about 10%, for example between about 1% to about 5% (by weight). In some embodiments, the surfactants may be included in the coating. In some other embodiments, the surfactants can be used as a compressibility augmenting agent. One skilled in the art, with the benefit of this disclosure, will understand that other components may be included to enhance one or more properties of the formulation. For example, the orally dissolving formulations according to the present invention may include disintegrating agents, antifoaming agents, antioxidants, buffering agents or coloring agents.

In some aspects, an anti-adherent or glidant of the present disclosure may include talc, magnesium silicate, colloidal silicon dioxide, amorphous silicon dioxide and calcium silicate. In some aspects, anti-adherent and glidant compounds may be used in an amount of about 0.1-5% by weight.

In some aspects, the orally dissolving formulations of the present invention may comprise an emulsifying agent as an excipient. As used herein, emulsifying agents include both solubilizers and wetting agents. Suitable emulsifying agents include, but are not limited to, polyvinyl alcohol, sorbitan esters, cyclodextrins, benzyl benzoate, glyceryl monostearate, polyoxyethylene alkyl ethers, polyoxyethylene stearates, poloxamer, polyoxyethylene castor oil derivatives (Cremophor), hydrogenated-vegetable oils, bile salts, polysorbates, ethanol or combinations thereof. The emulsifying agent can improve the compressibility during wet granulation process during manufacture.

In some embodiments, the orally disintegrating formulations or SMEDDS of the present invention may comprise a sweetening or flavoring agent. Generally, any natural or synthetic flavoring agent or sweetening agent known in the art may be used in the orally disintegrating or dissolving formulations of the present invention. For example, sweetening or flavoring agents include, but are not limited to, essential oils, water soluble extracts, sugar, monosaccharides, oligosaccharides, aldose, ketose, dextrose, maltose, lactose, glucose, fructose, sucrose, mannitol xylitol, D-sorbitol, erythritol, pentitol, hexitol, malitol, acesulfame potassium, talin, glycyrrhizin, sucralose, aspartame, saccharin, sodium saccharin, sodium cyclamate, eugenyl formate aldehyde flavorings and combinations thereof.

The disintegrant or "disintegrating agent" that may be employed as compositions of the invention may be defined as any material that is capable of accelerating to a measurable degree the disintegration/dispersion of a composition of the invention. The disintegrant may thus provide for an in vitro disintegration time of about 30 seconds or less, as measured according to e.g., the standard United States Pharmacopeia (USP) disintegration test method (see FDA Guidance for Industry: Orally Disintegrating Tablets; December 2008). This may be achieved, for example, by the material being capable of swelling, wicking and/or deformation when placed in contact with water and/or mucous (e.g., saliva), thus causing tablet formulations to disintegrate when so wetted. Suitable disintegrants (as defined in, for example, Rowe et al, Handbook of Pharmaceutical Excipients, 6th ed. (2009)) include cellulose derivatives such as hydroxypropyl cellulose (HPC), low substituted HPC, methyl cellulose, ethyl hydroxyethyl cellulose, carboxymethyl cellulose calcium, carboxymethyl cellulose sodium, microcrystalline cellulose, modified cellulose gum; starch derivatives such as moderately cross-linked starch, modified starch, hydroxylpropyl starch and pregelatinized starch; and other disintegrants such as calcium alginate, sodium alginate, alginic acid, chitosan, colloidal silicon dioxide, docusate sodium, guar gum, magnesium aluminum silicate, polacrilin potassium and polyvinylpyrrolidone. Combinations of two or more disintegrants may be used. Disintegrants include so-called "superdisintergrants" (as defined in, for example, Mohanachandran et al, International Journal of Pharmaceutical Sciences Review and Research, 6, 105 (2011)), such as cross-linked polyvinylpyrrolidone, sodium starch glycolate, calcium silicate, and croscarmellose sodium. Combinations of two or more superdisintegrants may be used. Disintegrants may also be combined with superdisintegrants in compositions of the invention. Disintegrants and/or superdisintegrants are preferably employed in an (e.g., total) amount of between 0.5 and 15% by weight based upon the total weight of a composition, e.g., from 1 to 8%, such as from about 2 to about 7% (e.g., about 5%, such as about 4%) by weight.

In some embodiments, the orally disintegrating formulations of the present invention may comprise a weak acid, or particles comprising weakly-acidic buffer forming materials. Weakly-acidic buffer forming materials include materials that, when provided in a composition of the invention, provide a weakly acidic buffer system when the composition is dissolved in water and/or saliva (e.g. at the site of administration of compositions of the invention), enabling the provision of a pH of between about 4.0 and about 6.5 (e.g. about 6.25), and are present in a sufficient amount to enable the maintenance of pH within this range for an appropriate length of time (e.g. about 30 seconds, such as about 1 minute) to about 3 minutes (e.g. about 2 minutes, such as about 1.5 minutes) to facilitate dissolution of, particularly, the ticagrelor and second agent, and/or absorption of ticagrelor and second agent across the oral mucosa thereafter. The weakly acidic material comprises a weak acid that is safe for human consumption, for example a food acid, such as malic acid, fumaric acid, adipic acid, caprylic acid, succinic acid, lactic acid, acetic acid, oxalic acid, maleic acid, ammonium chloride, preferably tartaric acid, and more preferably citric acid, or a combination of such acids.

Particles sizes of weakly acidic, or weakly-acidic buffer forming, materials are in the range about 1 pm and about 10,000 pm. Suitable amounts of weakly acidic materials that enable the maintenance of pH within the aforementioned ranges after oral administration as hereinbefore described are in the range of at least about 1% to about 10% by weight of the total formulation. Suitable total amounts of weakly-acidic buffer forming materials that enable the maintenance of pH within the aforementioned ranges after oral administration as hereinbefore described are in the range of at least about 1% to about 15% by weight of the total formulation.

In various embodiments, the orally disintegrating tablet has a hardness of about 20 N to about 100 N and friability of 5%, 4%, 3%, 2%, 1%, 0.5%, 0.4%, 0.3%, or 0.2% or less. In other embodiments, the ODT substantially disintegrates in an oral cavity of a subject in need thereof within less than about 20, 15, 10, 5, 1, 0.5 minutes after administration. The disintegration can be measured in vitro using e.g., the USP <701> Disintegration Test.

In some aspects, the ODT or ODF or SMEDDS releases at least 75%, at least 80%, at least 85%, at least 90%, at least 92%, at least 93%, at least 95%, at least 96%, at least 97%, at least 98%, or at least 99% of the ticagrelor or pharmaceutically acceptable salt thereof within 5, 10, 15, or 20 minutes using a standard dissolution test. For example, the dissolution may be measured with a dissolution apparatus USP 2 (paddles) using a suitable dissolution medium, e.g., water at pH 7.0, Phosphate buffer pH 6.8 (50 mM), or simulated human saliva at pH 6.8. The volume may be 500 mL. The temperature may be 37.0±0.5° C. The speed may be 50 rpm. The total time of dissolution may be sampled at 5, 10, 15, 20, 30, 60, 120, 360, 480, 720, and 960 minutes.

In some aspects, the ODT or ODF or SMEDDS releases at least 75%, at least 80%, at least 85%, at least 90%, at least 92%, at least 93%, at least 95%, at least 96%, at least 97%, at least 98%, or at least 99% of the magnesium or zinc compound or salt within 5, 10, 15, or 20 minutes using a standard dissolution test.

In some aspects, the ODT or ODF or SMEDDS releases at least 75%, at least 80%, at least 85%, at least 90%, at least 92%, at least 93%, at least 95%, at least 96%, at least 97%, at least 98%, or at least 99% of the magnesium or zinc compound or salt within 5, 10, 15, or 20 minutes using a simulated saliva fluid at pH about 6.8.

In some aspects, about 40, 45, 50, 55, 60, 65, 70, 75, 80, 85, 90, 95% or more of the maximum concentration of ticagrelor and about 50% or more of the maximum concentration of second active agent are absorbed in vivo into the plasma of a human subject within 1 hour after administering. In some aspects, about 70, 75, 80, 85% or more of the maximum concentration of ticagrelor and about 70% of the maximum concentration of second active agent are absorbed in vivo into the circulation plasma of a human subject within 6 hours after administering. In some aspects, about 80, 85, 90, 95% or more of the maximum concentration of ticagrelor and about 80% or more of the maximum concentration of second active agent are absorbed in vivo into the circulation plasma of a human subject within 8 hours after administering. In some aspects, an ODT or ODF of the present disclosure provides a therapeutically effective amount of ticagrelor to the brain of a subject within 1 hour of oral ingestion by the subject.

In some aspects, at least 25%, 30%, 35%, 40%, 45%, 50%, 55%, 60% or more of the ticagrelor and/or second agent in the ODT or ODF or SMEDDS is absorbed through the oral mucosa (e.g., sub- or supralingual or buccal).

The present disclosure provides an ODT or ODF or SMEDDS having structure and physical properties suitable for minimizing liver metabolism, gastrointestinal metabolism, delivering a more consistent dose to the brain, and avoiding cardiac effects of ticagrelor. Accordingly, the present disclosure provides a method of administering transmucosally. The present disclosure provides an ODT or ODF or SMEDDS having physical properties such that the active compounds are rapidly absorbed and pass directly into the bloodstream. Accordingly, the ODT and ODF or SMEDDS of the present disclosure can pass the drug quickly to the subject's brain rather than through gastric breakdown and liver metabolism.

In some aspects, the ODT or ODF or SMEDDS has a water absorption ratio of at least 40%, 50%, 55%, 60%, 65%, 70% or higher. In some aspects, the ODT or ODF has a wetting time of 10, 15, 20, 25, 30, 35, 40, 45, 50, 55, 60, or 65 seconds.

In some aspects, the ODT or ODF has tensile strength of 4, 4.5, 5, 5.5, 6, 6.5 N/cm$^2$, or higher. In some aspects, the ODT or ODF has a porosity of 15, 20, 25, 30, 35, 40, 45, 50% or higher.

In some aspects, the ODT has hardness of 30, 35, 40, 45, 50, 55, 60 N, or higher. In some aspects, the ODT has a thickness of 0.5, 1, 1.5, 2, 2.5, or 3 mm. In some aspects, the ODT or ODF has a total tablet weight of 200, 250, 300, 350, 400, 450, 500, 550, 600, 650, 700, 750, 800, 850, 900, 950, or 1000 mg.

In order to provide such physical properties, the ODT and ODF of the present disclosure contain a combination of ingredients that maximizes solubility of the ticagrelor in the oral cavity. While compounds such as magnesium, zinc, lysine, and lecithin can decrease solubility of ticagrelor, the present disclosure provides ODTs and ODFs having structures and components that provide high solubility of ticagrelor and satisfactory good taste and mouthfeel to maintain patient compliance or adherence to the dosing regimen, while also providing the disclosed pharmacokinetic and bioavailability characteristics to provide the desired therapeutic effect. In some aspects, the ODT or ODF has a pH of 5.5 to 7, e.g., 5.5, 5.6, 5.7, 5.8, 5.9, 6, 6.1, 6.2, 6.3, 6.4, 6.5, 6.6, 6.7, 6.8, 6.9, or 7.0 when dissolved in the oral cavity of a human, in deionized water, or in simulated human saliva.

In some aspects, the present disclosure includes a use or method of treating a subject having an Autism Spectrum Disorders, an intellectual disability, epilepsy, an anxiety disorder, a mood disorder, a disorder of social interaction, irritability, aggression, self-injurious behavior, hyperactivity, inattention, or Fragile X syndrome by administering ticagrelor, an enantiomer thereof, or a pharmaceutically acceptable salt thereof according to the present disclosure alone or in combination with a second agent of the present disclosure. The ticagrelor, an enantiomer thereof, or a pharmaceutically acceptable salt thereof may be co-administered with the second agent. The co-administration may include any suitable manner of administrating the ticagrelor, an enantiomer thereof, or a pharmaceutically acceptable salt thereof with the second agent. In some cases, the compounds are present in the same dosage form or in first and second dosage forms that are administered at the same time. In some cases, the first dosage form is administered after the second dosage form, or the second dosage form is administered after the first dosage form. In some cases, the first and second dosage forms are administered in alternating sequence. In some aspects, the present disclosure includes a use or method of treating a subject having an Autism Spectrum Disorders, an intellectual disability, epilepsy, an anxiety disorder, a mood disorder, a disorder of social interaction, irritability, aggression, self-injurious behavior, hyperactivity, inattention, or Fragile X syndrome by administering an ODT or ODF or SMEDDS of the present disclosure. In one aspect, the amount by weight of ticagrelor to be administered per day according to the methods of the present disclosure are less than for conventional ticagrelor regimens, e.g., less than 180 mg/day, less than 120 mg/day, less than 100 mg/day, less than 90 mg/day, less than 80 mg/day, less than 60 mg/day, less than 40 mg/day, less than 30 mg/day, less than 20 mg/day, or less than 10 mg/day. In some aspects, the present disclosure includes methods of co-administering ticagrelor with acetylsalicylic acid. In some aspects, the co-administering involves 5 mg to 300 mg, 10 to 280 mg, 20 to 260 mg, 30 to 250 mg, 40 to 200 mg, 50 to 180 mg, 60 to 160 mg, 70 to 150 mg, 80 to 140 mg, 90 to 130 mg, 75 to 100 mg, or less than 100 mg acetylsalicylic acid.

In some aspects, the methods of the present disclosure will decrease behavioral problems on the Aberrant Behavior Checklist (ABC-C). The ABC-C is a global behavior checklist that measures drug and other treatment effects in people with developmental disabilities. It is made up of five subscales, including Irritability, Lethargy, Inappropriate Speech, Hyperactivity, and Stereotypy based on 58 items that describe various behavioral problems.

In some aspects, the methods of the present disclosure will behavioral problems on the Clinical Global Impression Scale (CGI). The CGI is used by the study psychiatrist to judge the overall clinical condition relative to baseline using the same scale as the CGI-S. The study psychiatrist will rate the improvement from baseline. The CGI consists of a 7-point subjective scale assessing symptom. On this scale, scores of 1, 2, and 3 represent normal, some presence of symptoms, and mild behavior, respectively. A score of 4 represents moderate behavior. Scores of 5, 6, and 7 represent marked, severe, and among the most severe behavior, respectively.

In some aspects, the methods of the present disclosure will behavioral problems on the Modified Overt Aggression Scale (IBR-MOAS). The IBR-MOAS is a questionnaire that includes 5 types of aggression (verbal aggression towards self and others, physical aggression towards objects, self, and others) with four levels of severity for each type of aggression. Only the section assessing the 5 types of aggression will be used for repeat evaluations: Verbal aggression toward others, Verbal aggression toward self, Physical aggression against other people, Physical aggression against objects, Physical aggression against self. The frequency of occurrence of each item are as follows: 0=Never (never happens); 1=Rarely (averages about once a year to once a month); 2=Sometimes (averages about several times a month to several times a week); 3=Often (averages about daily to several times a day); and U (Used to happen but not this past year).

In some aspects, the methods of the present disclosure will behavioral problems on Questions About Behavior Function (QABF) measures. The QABF is an indirect assessment of behavioral function for individuals with developmental disabilities. It contains 25 items. The QABF yields five behavioral function categories: Access to Attention, Escape from Demands, Physical, Access to Tangible, and Nonsocial (i.e., sensory or automatically-maintained). Each question is scored with frequency descriptors of Never, Rarely, Some, and Often. A function is endorsed if the score for a particular function is at or above 4 points or higher.

In certain aspects, the specific dosing regimen involves administering the pharmaceutical composition to achieve or maintain a ticagrelor plasma level in a range of about 50-1000 ng/mL, 100-800 ng/mL, about 120-700 ng/mL, about 140-600 ng/mL, about 160-520 ng/mL, about 180-500 ng/mL, about 200-480 ng/mL, about 220-460 ng/mL, about 240-420 ng/mL, about 260-400 ng/mL, or about 500 ng/mL, about 530 ng/mL, about 560 ng/mL, about 580 ng/mL, about 600 ng/mL, or about 620 ng/mL. In some aspects, the dose level is aimed at reaching plasma levels of 1-1000 ng/ml, 2 hours after administration. In some aspects, the ticagrelor or pharmaceutically acceptable salt thereof such that a ticagrelor plasma level of about 50-300 ng/mL is maintained for at least 1, 2, 3, 4, 5, or 6 hours. In some aspects, the ticagrelor or pharmaceutically acceptable salt thereof such that a ticagrelor plasma level of about 30-50 ng/mL is maintained for at least 1, 2, 3, 4, 5, or 6 hours.

Oral dosing of ticagrelor in humans over 18 years is 5, 10, 20, 30, 40, 50, 60, 70, 80, 90, 100, 110, 120, 130, 140, 150, 160, 170, 180, 190, or 200 mg, e.g., 60 to 180 mg ticagrelor, e.g., once or twice daily. In some aspects, the dosage regimen may be increased at weekly intervals according to response For humans aged 18 and under, doses may be in a range of 0.1-3 mg/kg bodyweight one, two, three, or four times daily.

A method of safely delivering the combination of the present disclosure to a subject can include measuring electrocardiogram, pulse, and blood pressure of the subject before, during, and/or after the administering. Additionally, a method of safely delivering the combination of the present disclosure to a subject can include measuring liver enzyme levels while continuing administration of the combination. In certain aspects, steps can be taken to protect kidney, liver, intestines, or heart if the liver enzyme levels are abnormal, e.g., due to transient transaminase elevations. In some instances, the method further includes the preliminary step of measuring the subject's liver enzyme levels prior to administration. This can be done to establish a baseline liver enzyme level. The method can also include measuring liver enzyme levels at specified time periods after starting the administering step. In some embodiments, the subject's liver enzyme levels can be monitored at 4-hour intervals, 6-hour intervals, 8-hour intervals 12-hour intervals, 24-hour intervals, etc. Alternatively, levels can be checked at about 12 hours, about 24 hours, about 36 hours, about 48 hours, about 60 hours, about 72 hours, about 84 hours, about 96 hours, about 108 hours, about 120 hours, about 132 hours, about 154 hours, about 168 hours, the day the subject is discharged, or a combination thereof.

EXAMPLE 1

| Ingredients | Amount |
| --- | --- |
| Ticagrelor (mg) | 10 |
| Gelatin (mg) | 40 |
| Mannitol (mg) | 20 |
| Magnesium tartrate (mg) | 10 |
| Purified water | q.s. to 250 µl |

1) Dissolve Gelatin and other ingredients in purified water under stirring at 200-500 rpm.
2) Make up the final volume of the solution using purified water.
3) Mix the solution under stirring at 200 to 500 rpm for further 15 min.
4) Dose the solution into each cavity of preformed blister sheets (preferably using dispensing pipette).
5) Freeze the filled blisters at a temperature in the range of −20 to −110° C.
6) Freeze dry the blisters in a lyophilizer.
7) Place the blister sheet containing dried lyophilisates on the punched carrier web of the blister packaging machine to transport the blister sheets through the sealing station of the packaging machine
8) Seal the blister with a lidding foil and punch into final blisters.

EXAMPLE 2

| Ingredients | Amount |
| --- | --- |
| Ticagrelor (mg) | 10 |
| Gelatin (mg) | 40 |
| Mannitol (mg) | 20 |
| Methylparaben sodium (mg) | 10 |
| Propylparaben sodium (mg) | 10 |
| Zinc glycerate (mg) | 5 |
| Aspartame (mg) | 2 |
| Purified water | q.s. to 250 µl |

1) Dissolve Gelatin and other ingredients in purified water under stirring at 200-500 rpm.
2) Make up the final volume of the solution using purified water.
3) Mix the solution under stirring at 200 to 500 rpm for further 15 min.
4) Dose the solution into each cavity of preformed blister sheets (preferably using dispensing pipette).
5) Freeze the filled blisters at a temperature in the range of −20 to −110° C.
6) Freeze dry the blisters in a lyophilizer.
7) Place the blister sheet containing dried lyophilisates on the punched carrier web of the blister packaging machine to transport the blister sheets through the sealing station of the packaging machine
8) Seal the blister with a lidding foil and punch into final blisters.

EXAMPLE 3

| Ingredients | Weight (mg) |
| --- | --- |
| Ticagrelor | 10 |
| Avicel ® PH 102 | 50 |
| Sprayed dried lactose | 110 |
| Sodium starch glycolate | 4 |
| Crospovidone | 4 |
| Croscarmellose sodium | 4 |
| L-lysine | 10 |
| Talcum | 10 |
| Aspartame | 10 |

Mix the ingredients in the formulation and compress into tablets each with 5 mm in diameter and 2-3 mm in thickness by a single stroke tableting machine with the hardness between 3 to 5 kg. The thoroughly blended composition is compressed into plain tablets.

EXAMPLE 4

| Ingredients | Weight (mg) |
| --- | --- |
| Ticagrelor | 10 |
| Avicel ® PH 102 | 50 |
| Sprayed dried lactose | 100 |
| Sodium starch glycolate | 4 |
| Crospovidone | 4 |
| Croscarmellose sodium | 4 |
| Magnesium glycerate | 10 |
| Lecithin | 10 |
| Talcum | 10 |
| Aspartame | 10 |

Mix the ingredients in the formulation and compress into tablets each with 5 mm in diameter and 2-3 mm in thickness by a single stroke tableting machine with the hardness between 3 to 5 kg. The thoroughly blended composition is compressed into plain tablets.

EXAMPLE 5

| Ingredients | Amount |
| --- | --- |
| Ticagrelor (mg) | 70 |
| Pullulan (mg) | 400 |
| Propylene glycol (ml) | 0.25 |
| Polyvinyl pyrrolidone (mg) | 100 |
| Citric acid (mg) | 200 |
| Magnesium tartrate (mg) | 40 |
| Purified water (ml) | 20 |

Ticagrelor and pullulan are accurately weighed and dissolved in distilled water. This solution is mixed well followed by the addition of plasticizers and superdisintegrant.

Then the resultant homogeneous solution is poured into a Petri dish (diameter 6 cm) and dried in an oven at 600° C. for 24 h. The film is carefully removed from the Petri dish and cut into desired size (2×2 cm²).

EXAMPLE 6

| Ingredients | Amount |
| --- | --- |
| Ticagrelor (mg) | 70 |
| Pullulan (mg) | 400 |
| Propylene glycol (ml) | 0.25 |
| Polyvinyl pyrolidone (mg) | 100 |
| Citric acid (mg) | 200 |
| Zinc sulfate (mg) | 40 |
| Purified water (ml) | 20 |

Ticagrelor and pullulan were accurately weighed and dissolved in distilled water. This solution was mixed well followed by the addition of plasticizers and superdisintegrant. Then the resultant homogeneous solution was poured into a Petri dish (diameter 6 cm) and dried in an oven at 600° C. for 24 h. The film was carefully removed from the Petri dish and cut into desired size (2×2 cm2).

EXAMPLE 7

| Ingredients | Amount |
| --- | --- |
| Ticagrelor (mg) | 70 |
| Pectin(mg) | 200 |
| Mannitol(mg) | 100 |
| Carbopol(mg) | 300 |
| Citric acid (mg) | 100 |
| L-Lysine (mg) | 40 |
| Purified water (ml) | q.s. to 250 μl |

Ticagrelor and pullulan were accurately weighed and dissolved in distilled water. This solution was mixed well followed by the addition of plasticizers and superdisintegrant. Then the resultant homogeneous solution was poured into a Petri dish (diameter 6 cm) and dried in an oven at 600 C for 24 h. The film was carefully removed from the Petri dish and cut into desired size (2×2 cm2).

EXAMPLE 8

| Ingredients | Amount |
| --- | --- |
| Ticagrelor (mg) | 70 |
| Pullulan (mg) | 400 |
| Propylene glycol (ml) | 0.25 |
| Polyvinyl pyrrolidone (mg) | 100 |
| Citric acid (mg) | 200 |
| L-Lysine (mg) | 30 |
| Lecithin (mg) | 100 |
| Purified water (ml) | 20 |

Ticagrelor and pullulan were accurately weighed and dissolved in distilled water. This solution was mixed well followed by the addition of plasticizers and superdisintegrant. Then the resultant homogeneous solution was poured into a petri dish (diameter 6 cm) and dried in an oven at 600° C. for 24 h. The film was carefully removed from the petri dish and cut into desired size (2×2 cm²).

EXAMPLE 9

ODTs T1-T11 Further Exemplify Aspects of the Present Disclosure

| | T1 | T2 | T3 | T4 | T5 | T6 |
| --- | --- | --- | --- | --- | --- | --- |
| Active material | | | | | | |
| Ticagrelor free base or in complex with (1) | X | X | X | X | X | X |
| Magnesium salt with (2) | X | | | X | | |
| Zinc salt with (2) | | X | | | X | X |
| L-Lysine/L-arginine | | | X | | X | |
| Excipients | | | | | | |
| Acid (3) | X | X | X | | | X |
| Gelatin | X | X | | X | X | |
| Mannitol | X | X | | X | X | |
| Methylparaben sodium | | X | | | X | |
| Propylparaben sodium | | X | | | X | |
| Avicel ® PH 102 | | | X | | | X |
| Sprayed dried lactose | | | X | | | X |
| Sodium starch glycolate | | | X | | | X |
| Crospovidone | | | X | | | X |
| Croscarmellose sodium | | | X | | | X |
| Talcum | | | X | | | X |
| Taste making agents | | | | | | |
| Aspartame | | X | X | | X | X |
| Lecithin | | | X | | | X |

| | T7 | T8 | T9 | T10 | T11 |
| --- | --- | --- | --- | --- | --- |
| Active material | | | | | |
| Ticagrelor free base or in complex with (1) | X | X | X | X | X |
| Magnesium salt with (2) | | X | X | X | |
| Zinc salt with (2) | X | | | | X |
| L-Lysine/L-arginine | X | | X | | |
| Excipients | | | | | |
| Acid (3) | X | X | X | | |
| Gelatin | X | X | | X | X |
| Mannitol | X | X | | X | X |
| Methylparaben sodium | | | X | | |
| Propylparaben sodium | | | X | | |
| Avicel ® PH 102 | | | X | | |
| Sprayed dried lactose | | | X | | |
| Sodium starch glycolate | | | X | | |
| Crospovidone | | | X | | |
| Croscarmellose sodium | | | X | | |
| Talcum | | | X | | |
| Taste making agents | | | | | |
| Aspartame | | | X | X | |
| Lecithin | | | X | | |

(1) In complex with: hydrochloric acid, pyrophosphoric acid, tauric acid, sulfuric acid, acetic acid, carbonic acid, citric acid, ascorbic acid, threonic acid, tartaric acid, a malic acid, fumaric acid, gluconic acid, succinic acid, lactic acid, a glyceric acid, a glyceraldehyde, or an alpha-hydroxy-carboxylic acid.

(2) Salt form: sulphate, acetate, threonate, tartarate, glycerate, citrate, caprylate, chloride, sulfate, lactate, carbonate, malate, taurate, gluconate, succinate, or pyrophosphate.

(3) Acids: tartaric acid, glyceric acid, threonic acid, caprylic acid or gluconic acid.

The relative amounts of the ODT components are in accordance with the above-described aspects.

EXAMPLE 10

ODFs F1-F11 Further Exemplify Aspects of the Present Disclosure

|  | F1 | F2 | F3 | F4 | F5 | F6 |
|---|---|---|---|---|---|---|
| Active material | | | | | | |
| Ticagrelor free base or in complex with (1) | X | X | X | X | X | X |
| Magnesium salt with (2) | X | | | X | | |
| Zinc salt with (2) | | X | | | X | X |
| L-Lysine/L-arginine | | | X | | X | |
| Excipients | | | | | | |
| Acid (3) | X | X | X | | | X |
| Pullulan | X | | X | | X | |
| Propylene glycole | X | | X | | X | |
| Polyvinyl pyrrolidone | X | | X | | X | |
| Purified water | X | X | X | X | X | X |
| Pectin | | X | | X | | X |
| Mannitol | | X | | X | | X |
| Carbopol | | X | | X | | X |
| Taste making agents | | | | | | |
| Aspartame | X | | X | X | | X |
| Lecithin | | X | X | | | X |

|  | F7 | F8 | F9 | F10 | F11 |
|---|---|---|---|---|---|
| Active material | | | | | |
| Ticagrelor free base or in complex with (1) | X | X | X | X | X |
| Magnesium salt with (2) | X | X | | X | |
| Zinc salt with (2) | | | X | | X |
| L-Lysine/L-arginine | X | | | | |
| Excipients | | | | | |
| Acid (3) | X | X | | | |
| Pullulan | X | | | X | X |
| Propylene glycole | X | | | X | X |
| Polyvinyl pyrrolidone | X | | | X | X |
| Purified water | X | X | X | X | X |
| Pectin | | X | X | | |
| Mannitol | | X | X | | |
| Carbopol | | X | X | | |
| Taste making agents | | | | | |
| Aspartame | X | X | X | | |
| Lecithin | X | | X | | |

(1) In complex with: hydrochloric acid, pyrophosphoric acid, tauric acid, sulfuric acid, acetic acid, caprylic acid, carbonic acid, citric acid, ascorbic acid, threonic acid, tartaric acid, a malic acid, fumaric acid, gluconic acid, succinic acid, lactic acid, a glyceric acid, a glyceraldehyde, or an alpha-hydroxy-carboxylic acid.
(2) Salt Form: sulphate, acetate, threonate, tartarate, glycerate, caprylate, citrate, chloride, sulfate, lactate, carbonate, malate, taurate, gluconate, succinate, or pyrophosphate.
Acids: tartaric acid, glyceric acid, threonic acid, caprylic or gluconic acid.
The relative amounts of the ODF components are in accordance with the above-described aspects.

EXAMPLE 11

A self-microemulsifying formulation (total weight: 800 mg) modified from (Na et al. Strategic approach to developing a self-microemulsifying drug delivery system to enhance antiplatelet activity and bioavailability of ticagrelor. Int J Nanomedicine. 2019 Feb. 15; 14:1193-1212; CN104971042A; and KR102007731B1 (each of which is incorporated herein by reference in its entirety)), was prepared by mixing, an oil (Capmul MCM; 45.0 w/w %), surfactant agent (Cremophor EL; 38 w/w %) and a co-surfactant (Transcutol P; 17 w/w %). The mixture was gently stirred to make a uniform solution, then, 100 mg ticagrelor and 100 mg zinc caprylate were added and mixed to make a uniform formulation. Each drop of the mixture contains 5 mg of ticagrelor and 5 mg of zinc caprylate.

| Ingredients | Amount (mg) |
|---|---|
| Ticagrelor (mg) | 100 |
| Zinc caprylate (mg) | 100 |
| Capmul MCM (mg) | 360 |
| Cremophor EL (mg) | 304 |
| Transcutol P(mg) | 136 |

EXAMPLE 12

SMEDDS S1-S11 Further Exemplify Aspects of the Present Disclosure

|  | S1 | S2 | S3 | S4 | S5 | S6 |
|---|---|---|---|---|---|---|
| Active material | | | | | | |
| Ticagrelor free base or in complex with (1) | X | X | X | X | X | X |
| Magnesium salt with (2) | X | | | X | | |
| Zinc salt with (2) | | X | | | X | X |
| L-Lysine/L-arginine | | | X | | X | |
| Excipients | | | | | | |
| Caprylic acid | X | X | X | | | X |
| Capric acid | X | | X | X | | |
| Glycerol Monocaprylocaprate | X | | | X | X | |
| Polyoxyethylated castor oil | X | | X | | X | |
| Polyoxyethylene sorbitan fatty acid | X | X | X | X | X | X |
| Diethylene glycol monoethyl ether | X | X | | | X | X |
| Tetraglycol | | X | X | X | | X |
| Taste making agents | | | | | | |
| Aspartame | X | | X | X | | X |
| Lecithin | | X | X | | | X |

|  | S7 | S8 | S9 | S10 | S11 |
|---|---|---|---|---|---|
| Active material | | | | | |
| Ticagrelor free base or in complex with (1) | X | X | X | X | X |
| Magnesium salt with (2) | X | X | | X | |
| Zinc salt with (2) | | | X | | X |
| L-Lysine/L-arginine | X | | | | |
| Excipients | | | | | |
| Caprylic acid | X | X | | | |
| Capric acid | X | | | X | X |
| Glycerol Monocaprylocaprate | X | | | X | X |
| Polyoxyethylated castor oil | X | | | X | X |
| Polyoxyethylene sorbitan fatty acid | X | X | X | X | X |
| Diethylene glycol monoethyl ether | | | X | X | |
| Tetraglycol | | | | X | X |
| Taste making agents | | | | | |
| Aspartame | X | X | X | | |
| Lecithin | X | | X | | |

EXAMPLE 13: IN VIVO EXPERIMENT: —THE VALPROIC ACID (VPA) MODEL OF AUTISM

Exposure to valproic acid (VPA) during pregnancy has been demonstrated to increase the risk of autism in children. Furthermore, rodents prenatally exposed to this drug display behavioral phenotypes characteristics of the human autism condition. This model might better represent the many cases of idiopathic autism which are of environmental/epigenetic origins than do transgenic models carrying mutations in single autism-associated genes. The VPA model is an environmentally triggered model with strong construct and clinical validity. The VPA-induced rodent model is an art-recognized and well-established and widely utilized animal model to test putative efficacy of pharmacological agents on behavioral and social elements in the autistic spectrum for humans.

C57BL/6J mice were obtained at 7-8 weeks of age and were mated, with pregnancy confirmed by the presence of a vaginal plug on embryonic day 0 (E0). On E12.5, pregnant females received a single intraperitoneal injection of sodium salt of valproic acid (VPA, 500 mg/kg) dissolved in saline (SAL). Control females received an equal volume of SAL only. Day of birth was recorded as P0 (postnatal day zero). The offspring were weaned on P21 (postnatal day 21) and the male offspring were housed in groups of 4-5. Experiments were carried out on male offspring. The mice were housed in a temperature- and humidity-controlled environment with ad libitum access to food and water. Animals were maintained on a 12 hr light/dark schedule, with lights on at 8 A.M.

The male offspring of VPA-treated mice were divided into 4 groups (n=8-9 per group): VPA-Vehicle)+50 µg of ZnSO4, VPA-ticagrelor (0.3 mg/kg)+50 µm of ZnSO4, VPA-ticagrelor (10 mg/kg)+50 µg of ZnSO4 and VPA-ticagrelor (30 mg/kg)+50 µg of ZnSO4. The male offspring of SAL-treated mice were divided into 2 groups (n=10 per group): SAL-Vehicle and SAL-ticagrelor (30 mg/kg)+50 µg of ZnSO4. From the sixth week to eight week of age, the mice received three once-weekly injections of either saline (50 µl/g ip) or ticagrelor (i.p.). Twenty-four hours after the last injection, the three chamber test was performed.

Behavioral Assay—Three Chamber Test

The three-chamber test assesses cognition in the form of general sociability and interest in social novelty in a rodent model of CNS disorders. This test measures the sociability, the propensity to spend time with another mouse, as compared to time spent alone in an identical but empty chamber.

The apparatus was an acrylic box (length: 62 cm, width: 41 cm, height: 30.5 cm) divided into three chambers. A 5 cm×5 cm opening was made on the partitions so that mice could freely explore the three chambers. Mouse was first placed into the centre chamber of the apparatus and allowed 5 min for habituation. Following the completion of the acclimatization period the test mouse was removed to a holding cage, and the bedding material was redistributed. Then a novel mouse enclosed in a tiny cage was placed in one lateral chamber (social area) and an empty tiny cage was placed in the other lateral chamber as a novel object (non-social area). Mouse was first placed into the centre chamber and allowed to freely explore the chambers for 10 min and the time spent in each of the three areas (social, centre, and non-social areas) was recorded.

Statistical Analyses: Statistical analyses for the data were performed using one-way or two-way RM ANOVA (SigmaStat 3.1). Post-hoc comparisons were performed with the Tukey HSD method. If data were not normally distributed, Kruskal-Wallis one way ANOVA on ranks followed by the Dunn's method was used. All data were represented as mean±SEM. Significant level was set at $p<0.05$.

Results: A one-way ANOVA of the time spent in social area revealed a significant difference among the six groups ($F(5, 48)=5.201$, $p<0.001$). Post hoc comparisons showed that compared with the SAL-Vehicle group, the VPA-Vehicle group showed a significant decrease of the time spent in social area ($p<0.05$) (FIG. 1, left panel). Compared with the VPA-Vehicle group, both the VPA-ticagrelor (10 mg/kg) and VPA-ticagrelor (30) groups showed a significant increase of the time spent in social area ($p<0.01$ and $p<0.001$). There was no significant difference in the time spent in social area between the SAL-Vehicle group and the SAL-ticagrelor (30) group ($p>0.05$).

A one-way ANOVA of the time spent in centre area revealed a significant difference among the six groups ($F(5, 48)=3.821$, $p<0.01$). Post hoc comparisons showed that compared with the VPA-Vehicle group, the VPA-ticagrelor (30) group showed a significant decrease of the time spent in centre area ($p<0.05$) (FIG. 1, centre panel).

A one-way ANOVA of the time spent in non-social area revealed a significant difference among the six groups ($F(5, 48)=5.230$, $p<0.001$). Post hoc comparisons showed that compared with the SAL-Vehicle group, the VPA-Vehicle group showed a significant increase of the time spent in non-social area ($p<0.01$) (FIG. 1, right panel). Compared with the VPA-Vehicle group, both the VPA-ticagrelor (10 mg/kg) and VPA-ticagrelor (30 mg/kg) groups showed a significant decrease of the time spent in non-social area (both, $p<0.01$). There was no significant difference in the time spent in non-social area between the SAL-Vehicle group and the SAL-ticagrelor (30 mg/kg) group ($p>0.05$).

Conclusions: Three once-weekly administration of ticagrelor and zinc salt attenuated the deficit in sociability, an autism-relevant symptom, displayed by the in utero exposed to VPA C57BL/6J mice. Impairments were observed in the 3-chamber test of the VPA group compared to the control mice. In contrast, ticagrelor-treated groups, at the doses of 10 and 30 mg/kg, presented a significant increase in time spent near the cage with the stimulus mouse ("social" area). The data show a postnatal effect of ticagrelor in a relevant autism animal model that is indicative of enhanced sociability deficits in autistic patients.

Any of the above protocols or similar variants thereof can be described in various documentation associated with a pharmaceutical product. This documentation can include, without limitation, protocols, statistical analysis plans, investigator brochures, clinical guidelines, medication guides, risk evaluation and mediation programs, prescribing information and other documentation that may be associated with a pharmaceutical product. It is specifically contemplated that such documentation may be physically packaged with an ODT or ODF pharmaceutical product according to the present disclosure as a kit, as may be beneficial or as set forth by regulatory authorities.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations are not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method of treating a subject diagnosed with an autism spectrum disorder, an intellectual disability, epilepsy, an anxiety disorder, a mood disorder, a disorder of social interaction, irritability, aggression, self-injurious behavior, hyperactivity, inattention, Fragile X syndrome, or diagnosed with elevated TNFα, or diagnosed with elevated inflammatory cytokine marker of neuroinflammation comprising administering ticagrelor, an enantiomer thereof, or a pharmaceutically acceptable salt thereof to the subject or administering a combination of ticagrelor, an enantiomer thereof, or a pharmaceutically acceptable salt thereof with a second agent in a weight ratio of 1:0.1 to 1:50 to the subject, wherein the administering does not include administering antioxidants.

2. The method of claim 1, comprising administering the ticagrelor or the combination orally or parenterally.

3. The method of claim 1, comprising administering less than 60, 40, 30, or 20 mg/day of the ticagrelor, enantiomer or pharmaceutically acceptable salt thereof.

4. The method of claim 1, comprising delivering the ticagrelor, enantiomer or pharmaceutically acceptable salt thereof such that a ticagrelor plasma level is sufficient to treat autism symptoms in a subject.

5. The method of claim 4, wherein a ticagrelor plasma level of about 50-300 ng/mL is achieved in the subject.

6. The method of claim 4, comprising delivering the ticagrelor, enantiomer or pharmaceutically acceptable salt thereof such that a ticagrelor plasma level sufficient to treat autism symptoms in a child or adult is maintained for at least 5 hours.

7. The method of claim 6, wherein the maintained ticagrelor plasma level is about 50-300 ng/mL.

8. The method of claim 1, further comprising maintaining a ticagrelor plasma level of about 50-300 ng/mL for at least 7 hours.

9. The method of claim 1, further comprising maintaining a ticagrelor plasma level of about 80-200 ng/mL for at least 5 hours.

10. The method of claim 1, further comprising maintaining a ticagrelor plasma level of about 80-200 ng/mL for at least 7 hours.

11. The method of claim 1, comprising administering the ticagrelor or the combination orally.

12. The method of claim 11, wherein the orally administering is via a solid orally disintegrating tablet (ODT) or a solid orally dissolving film (ODF) or a Self-microemulsifying drug delivery system (SMEDDS).

13. The method of claim 11, wherein the orally administering is via a solid orally disintegrating tablet (ODT).

14. The method of claim 11, wherein the orally administering is via a solid orally dissolving film (ODF).

15. The method of claim 11, wherein the orally administering is via a Self-microemulsifying drug delivery system (SMEDDS).

16. The method of claim 1, wherein the subject is diagnosed with an anxiety disorder.

17. The method of claim 1, wherein the subject is diagnosed with irritability, aggression, self-injurious behavior, hyperactivity, or inattention.

18. The method of claim 1, wherein the subject is diagnosed with Fragile X syndrome.

19. The method of claim 1, wherein the subject is diagnosed with elevated TNFα.

20. The method of claim 1, wherein the subject is diagnosed with an elevated inflammatory cytokine marker of neuroinflammation.

21. A method of treating a subject diagnosed with an autism spectrum disorder, an intellectual disability, epilepsy, an anxiety disorder, a mood disorder, a disorder of social interaction, irritability, aggression, self-injurious behavior, hyperactivity, inattention, Fragile X syndrome, or diagnosed with elevated TNFα, or diagnosed with elevated inflammatory cytokine marker of neuroinflammation comprising administering a combination of ticagrelor, an enantiomer thereof, or a pharmaceutically acceptable salt thereof with a second agent in a weight ratio of 1:0.1 to 1:50 to the subject, wherein the second agent is selected from the group consisting of a magnesium ion containing-compound, a zinc ion containing-compound, L-lysine or a salt thereof, L-arginine or a salt thereof, lecithin, or a combination thereof.

22. The method of claim 21, comprising administering the ticagrelor or the combination orally.

23. The method of claim 21, wherein the second agent is a magnesium ion containing-compound.

24. The method of claim 21, wherein the second agent is a zinc ion containing-compound.

25. The method of claim 21, wherein the second agent is L-lysine or a salt thereof.

26. The method of claim 21, wherein the second agent is L-arginine or a salt thereof.

27. The method of claim 21, wherein the second agent is lecithin.

28. A method of treating a subject diagnosed with an intellectual disability, irritability, aggression, self-injurious behavior, hyperactivity, inattention, Fragile X syndrome, or diagnosed with elevated TNFα, or diagnosed with elevated inflammatory cytokine marker of neuroinflammation comprising administering ticagrelor, an enantiomer thereof, or a pharmaceutically acceptable salt thereof to the subject or administering a combination of ticagrelor, an enantiomer thereof, or a pharmaceutically acceptable salt thereof with a second agent in a weight ratio of 1:0.1 to 1:50 to the subject, wherein the second agent is selected from the group consisting of a magnesium ion containing-compound, a zinc ion containing-compound, L-lysine or a salt thereof, L-arginine or a salt thereof, lecithin, or a combination thereof.

* * * * *